United States Patent [19]

Coury et al.

[11] Patent Number: 4,820,289

[45] Date of Patent: Apr. 11, 1989

[54] MALE EXTERNAL CATHETER

[75] Inventors: Frank Coury, Highland Park; Margaret A. Frank, Lawrenceville; Daniel M. Sivilich, Freehold Township, Monmouth County, all of N.J.

[73] Assignee: E. R. Squibb & Sons, Inc., Princeton, N.J.

[21] Appl. No.: 102,080

[22] Filed: Sep. 29, 1987

[51] Int. Cl.$^4$ .............................................. A61F 5/44
[52] U.S. Cl. ..................................... 604/349; 427/181
[58] Field of Search .............. 604/346, 347, 348, 349, 604/351, 352, 353, 322, 327, 333, 337, 344; 427/180, 181

[56] References Cited

U.S. PATENT DOCUMENTS

| 3,349,768 | 10/1967 | Keane | 604/347 |
|---|---|---|---|
| 3,511,241 | 5/1970 | Lee | 604/352 |
| 3,520,305 | 7/1970 | Davis | 604/349 |
| 3,608,552 | 9/1971 | Broerman . | |
| 3,633,581 | 1/1972 | Welch | 604/351 |
| 3,788,324 | 1/1974 | Lim . | |
| 3,863,638 | 2/1975 | Rogers, III et al. . | |
| 4,035,532 | 7/1977 | Gregorian et al. | 427/331 |
| 4,187,851 | 2/1980 | Hauser . | |
| 4,419,097 | 12/1983 | Rowland | 604/352 |
| 4,475,909 | 10/1984 | Eisenberg . | |
| 4,475,910 | 10/1984 | Conway et al. . | |
| 4,483,951 | 11/1984 | Brenner | 524/82 |
| 4,490,145 | 12/1984 | Campbell | 604/333 |
| 4,573,984 | 3/1986 | Benzies | 604/339 |
| 4,601,716 | 7/1986 | Smith . | |
| 4,675,012 | 6/1987 | Rooyakkers | 604/349 |
| 4,726,359 | 2/1988 | Schroeder | 128/132 R |

FOREIGN PATENT DOCUMENTS 2099706 12/1982 United Kingdom ................ 604/349

Primary Examiner—C. Fred Rosenbaum
Assistant Examiner—Mario Costantino
Attorney, Agent, or Firm—Theodore R. Furman, Jr.

[57] ABSTRACT

A male external catheter comprising a condom-like sheath having at least one of its surfaces flocked with a fabric is disclosed. The flocked catheter provides greater comfort, absorbs moisture, and is easier to apply than prior art sheaths.

11 Claims, No Drawings

4,820,289

MALE EXTERNAL CATHETER

FIELD OF THE INVENTION

The present invention is related to male urinary evacuation and more particularly concerns an external male catheter and a method for its manufacture.

BACKGROUND OF THE INVENTION

External catheters used for male urinary evacuation, e.g in male incontinence devices and the like. typically comprise a sheath applied to the user's penis wherein the sheath has a constricted downstream end portion adapted for fluid-tight connection with a drain tube. The sheath is typically of a thin, elastomeric fluid-impermeable material such as latex rubber or silicone rubber. This sheath is essentially similar to a condom which can be rolled onto the penis.

Problems associated with such prior art external catheters include discomfort caused by prolonged contact of the rubber sheath with the penis, difficulty in maintaining the sheath in a sealably connected arrangement with the penis, and difficulty in unrolling the sheath onto the penis.

U.S. Pat. Nos. 3,863,638 to Rogers, III et al.; 4,187,851 to Hauser and 4,475,909 to Eisenberg describe similar methods for securing the sheath of such an external catheter to the penis in a comfortable manner.

Rogers, III et al. describe an adhesive pad which is wrapped around the penis at least 1.5 times. The pad serves to maintain contact between the sheath and the penis and also protects at least a portion of the penis from extended contact with the sheath.

Hauser has described a tape which is padded and which, by virtue of its lesser width when compared to the above-described Rogers, III et al. pad, is able to accommodate a broader range of sizes. The tape can be wrapped in a partially overlapping fashion to cover the area desired.

Eisenberg has eliminated the bulkiness caused by the overlap of Hauser and Rogers by designing an adhesive cushion which encircles the penis with no overlap necessary.

In all three of the above designs, the rubber sheath can still cause substantial skin irritation to that portion of the penis not protected by the tapes or pads described. Additionally, the outside of the sheath causes irritation to the thigh or crotch area with which it is usually in contact. Even small amounts of urine, in the areas where the sheath touches the skin, greatly augments the skin irritation.

U.S. Pat. No. 3,608,552 to Broerman describes a male urinal device wherein the sheath is fabricated by stretching a tubular woven fabric base over a suitable mold and dipping the same into a rubber compound which is liquid in its uncured state. The resulting sheath has enhanced rigidity due to the fabric base and comprises essentially a rubber impregnated fabric on its inside and the cured rubber on the outside. This less flexible sheath can result in leakage problems as the patient moves around. Additionally, the penis is still contacted to a large extent by the rubber of the sheath and the rubber outside of the sheath can still cause skin irritation to the thigh and/or crotch area.

SUMMARY OF THE INVENTION

In accordance with the present invention, an improved male external catheter, flocked with particles of fiber, providing greater comfort, flexibility and ease of use to the wearer is disclosed. The flocked external catheter comprises a sheath of a thin, flexible material having an inside surface and an outside surface, adapted to fit over the penis, and having a constricted downstream end portion adapted for a fluid-tight connection with a drain tube, wherein at least one of the surfaces further comprises a thin layer of adhesive and a uniform layer of small particles of a fabric bonded thereto.

Also disclosed is a method for fabricating the external catheter of the present invention which comprises forming the sheath of the desired shape and material, coating the surface or surfaces to be flocked with a thin layer of an adhesive, placing the so-coated sheath and a sufficient amount of flocking material comprising particles of fabric into a closed chamber, and establishing relative motion between the sheath and the flocking material so that the flocking material uniformly covers, and is bonded to, the adhesive coated surface.

DETAILED DESCRIPTION OF THE PRESENT INVENTION

The present invention provides numerous important advantages over the prior art sheath-like catheters and incontinence devices. First, the flocking provides a soft, comfortable surface which substantially reduces skin irritation. In addition to being more comfortable on dry skin, the flocked catheter provides greater comfort for areas of skin which typically become moist after extended usage, e.g. from perspiration or urine, due to the absorbent qualities of the flocking material. Further, the adhesive and flocking, even if on the inside and outside of the condom-like sheath, add almost nothing to the thickness of the present external catheter. Therefore, the external catheter of the present invention still provides a non-bulky, highly flexible sheath for urinary evacuation. Additionally, the present external catheter, whether flocked on one or both sides, is much easier to unroll onto the penis. This is because the high degree of surface tension which exists between the inside and outside rubber surfaces of a prior art sheath is drastically reduced by the presence of the flocking material. Correspondingly, removal of the present external catheter from moist skin is easier when utilizing a sheath flocked at least on the inside surface.

The flocking material also provides a better "hand" to the caregiver. Optionally, the flocking materials could be any convenient color for easier identification, especially by elderly patients.

The sheath of the present external catheter can be of any thin, flexible, elastomeric, moisture-impermeable material used in the prior art devices, such as latex rubber or silicone rubber. The sheath typically has a tube-like shape, like a condom, but with a constricted downstream end portion adapted to receive tubing which transfers the urine to a suitable receptacle.

The flocking material consists of very small particles of a fiber such as cotton, polyester, rayon, polypropylene, polyethylene and the like, including blends thereof. The flocking material chosen depends on the texture and absorbency qualities desired.

The adhesive coating may comprise any convenient adhesive which can be applied to the sheath in a thin uniform layer and will bond the particles of flocking material thereto. Acrylic adhesives, commercially available, which can be applied to the sheath by dipping or spraying, have been found extremely useful. Also, neoprene blends, or other adhesives which can be applied by dipping or spraying, are suitable.

The preparation of the flocked external catheter of the present invention will now be described by reference to a specific embodiment which contemplates the use of a latex rubber sheath. It will be apparent to those skilled in the art that any other prior art methods of forming the sheath may be employed.

First, a mold for the desired shape is dipped into a latex bath. After withdrawing the mold from the bath, while the so-formed sheath is still stretched onto the mold, the latex is allowed to dry and thereafter is coated with a thin layer of acrylic adhesive which can be done, for example, by spraying or by secondary dipping. While the adhesive is still tacky, the sheath is placed into a chamber, which preferably can accommodate a plurality of sheaths. A sufficient amount of particles of flocking material are also placed in the chamber. The chamber is an enclosed box-like unit having means for establishing relative motion between the sheath and the flocking material. Typically, this can be accomplished by a blower or fan which blows the particles of flocking material throughout the chamber, thereby causing the material to adhere to the adhesive-coated sheath in a uniform manner. However, any other convenient means for contacting the particles to the sheath may be employed. This provides an external catheter flocked on the outside surface only.

To prepare an external catheter flocked on the inside surface only, the latex sheath, as formed above, is removed from the mold after curing, drying and placed inside out over the mold or a similar form. The adhesive-coating and flocking steps described above are then followed.

To prepare an external catheter flocked on both sides, the outside-flocked catheter is merely turned inside out over a mold or similar form and the adhesive coating and flocking steps are repeated on the inside surface.

The flocked, external catheter provided by the present invention is a smooth, soft, felt-like sheath which feels cooler to the skin than latex rubber or silicone rubber in warm weather, warmer to the skin in cool weather and helps by absorbing moisture such as perspiration or urine. These comforts are accomplished without sacrificing the flexibility and thin, light-weight qualities provided by standard thin elastomeric sheaths.

It should be apparent that the flocked external catheter of the present invention can be conveniently employed by itself or in conjunction with any of the catheters, urinary evacuation systems, male incontinence devices or padded adhesive tapes in the prior art (such as those described above) which utilize such a sheath.

The invention will now be described by the following Example but should not be limited to the details therein.

EXAMPLE 1

An aluminum mold, specifically designed to yield the desired shape product, was dipped into a bath of coagulant calcium nitrate ($CaNO_3$). The mold was then air dried for 1.5 minutes. The coated mold was then dipped into a bath of liquid uncured latex rubber, removed and air dried for 10 minutes. The latex-coated mold was then water washed at 100° F. for 10 minutes, and air dried for 10 minutes. The coated mold was dipped into a liquid neoprene blend adhesive. The coated mold, while still tacky, was then introduced into a laboratory flocking chamber and submitted to a dusting of cotton flock. The mold was rotated by hand in the dust (flocking) stream to obtain a uniform application of flock. The flocked mold was then cured in an oven by gradually raising the temperature from 130° F. to 200° F. for 1 hour and then submitting the mold to a temperature of 245° F. for 0.5 hour.

What is claimed is:

1. In a male external condom catheter for use in male urinary evacuation or male incontinence, which catheter comprises a sheath of a thin, flexible, elastomeric material, having an inside surface and an outside surface, adapted to fit over the penis, and having a constricted downstream end portion adapted to provide a fluid-tight connection with a drain tube;

the improvement wherein at least one of said surfaces of said sheath is flocked wherein said flocking comprises a thin uniform layer of adhesive on said surface and a plurality of particles of a fiber uniformly covering, and bonded to, said adhesive such that a smooth felt-like surface is provided.

2. The external catheter of claim 1 wherein said thin, flexible, elastomeric material is selected from latex rubber and silicone rubber.

3. The external catheter of claim 2 wherein said material is latex rubber.

4. The external catheter of claim 1 wherein said flocking is selected from cotton, rayon, polyester, polypropylene, polyethylene and blends thereof.

5. The external catheter of claim 4 wherein said flocking is of rayon.

6. The external catheter of claim 1 wherein said adhesive is selected from neoprene blends and acrylic adhesives.

7. The external catheter of claim 6 wherein said adhesive is a neoprene blend.

8. A method for preparing a flocked male external condom catheter comprising
    (a) forming a sheath in the shape desired for said catheter;
    (b) applying a thin, uniform coating of adhesive to surfaces of said sheath to be flocked;
    (c) placing the so-coated sheath, prior to curing of said adhesive, into an enclosed chamber containing an amount of particles of a desired fabric flocking material sufficient to cover said surfaces to be flocked; and,
    (d) establishing relative motion between said sheath and said particles of fabric such that a uniform coating of said particles bonded to said adhesive coated sheath is provided.

9. The method of claim 8 wherein said sheath is formed by dipping a mold of the desired catheter shape into a bath of a flexible elastomeric material in a liquid, uncured state and thereafter removing said mold from said bath and allowing the so-formed sheath to cool and dry.

10. The method of claim 8 wherein said thin, uniform coating of adhesive is sprayed onto said sheath.

11. The method of claim 8 wherein the relative motion is established by blowing said flocking particles throughout said chamber.

* * * * *